United States Patent [19]

Čásenský et al.

[11] 4,124,584

[45] Nov. 7, 1978

[54] PROCESS OF MANUFACTURING SODIUM LACTAMOALUMINATES

[75] Inventors: Bohuslav Čásenský, Prague; Jiří Macháček, Kralupy; Otomar Kříž, Prague; Vladimir Kubánek, Kralupy, all of Czechoslovakia

[73] Assignee: Ceskoslovenska akademie ved, Prague, Czechoslovakia

[21] Appl. No.: 746,823

[22] Filed: Dec. 2, 1976

[30] Foreign Application Priority Data

Jul. 1, 1976 [CS] Czechoslovakia .................... 4352-76
Jul. 1, 1976 [CS] Czechoslovakia .................... 4351-76

[51] Int. Cl.$^2$ .................. C07D 223/10; C07D 211/86; C07D 207/26
[52] U.S. Cl. ..................... 260/239.3 R; 260/326.5 A; 260/448 AD; 252/431 R; 252/431 L; 252/431 N; 546/11; 528/317; 528/319
[58] Field of Search ................ 260/239.3 R, 270 PD, 260/448 AD, 326.5 A

[56] References Cited

U.S. PATENT DOCUMENTS

| | | | |
|---|---|---|---|
| 3,507,895 | 4/1970 | Casensky et al. | 260/448 AD |
| 3,674,751 | 7/1972 | Kralicek et al. | 260/239.3 R |
| 3,919,175 | 11/1975 | Kralicek et al. | 260/448 AD |

FOREIGN PATENT DOCUMENTS

46/31,534  9/1968  Japan ................................. 260/239.3 A

*Primary Examiner*—Henry R. Jiles
*Assistant Examiner*—Robert T. Bond
*Attorney, Agent, or Firm*—Burgess, Ryan and Wayne

[57] ABSTRACT

A process of manufacturing sodium lactamoaluminates by reacting an excess of a lactam in an aromatic hydrocarbon with at least one compound selected from sodium tetrahydridoaluminate, trisodium hexahydridoaluminate, sodium dihydrido-bis(2-methoxyethoxo)aluminate, and sodium tetraamidoaluminate.

8 Claims, No Drawings

PROCESS OF MANUFACTURING SODIUM LACTAMOALUMINATES

The invention relates to a process of manufacturing sodium lactamoaluminates of the general formula $$Na\,Al\,(OCH_2CH_2OCH_3)_x\,L_{4-x},$$

where $x$ is a number ranging from 0 to 2 and L is a residue derived by splitting off an active hydrogen from a lactam having the general formula

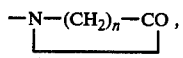

where $n$ is a number ranging from 3 to 11.

The best known compounds of lactams with metals are alkali metal lactamates which are produced by the reaction of lactams with alkali metals, their hydrides, hydroxides, or alkoxides, and used as initiators of anionic polymerization of lactams. The application of alkali metal lactamates for initiating the anionic polymerization presents some difficulties since the reaction mixture has to be freed of water and/or alcohol by distilling off the lactam heads under reduced pressure.

The afore-mentioned disadvantage is not encountered when sodium lactamoaluminates are used as initiators of anionic polymerization of lactams. These compounds, however, have not yet been produced on an industrial scale.

Accordingly, the object of this invention is to provide a technologically and economically effective process for the production of sodium lactamoaluminates.

Such process produces sodium lactamoaluminates of the general formula $$Na\,Al\,(OCH_2CH_2OCH_3)_x\,L_{4-x},$$

where $x$ is a number ranging from 0 to 2 and L is a residue derived by splitting off an active hydrogen from a lactam having the general formula

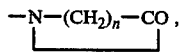

where $n$ is a number ranging from 3 to 11.

In the method of the invention, an excess of a lactam having the general formula LH, where L has the same meaning as mentioned above, is reacted in an aromatic hydrocarbon medium with at least one compound selected from the group comprising sodium tetrahydridoaluminate $NaAlH_4$, trisodium hexahydridoaluminate $Na_3AlH_6$, sodium dihydrido-bis(2-methoxyethoxo)aluminate $NaAlH_2(OCH_2CH_2OCH_3)_2$, and sodium tetraamidoaluminate $NaAl(NH_2)_4$. The molar ratio of the lactam to hydride hydrogen $H^-$ or $NH_2$-group contained in the aforementioned aluminates ranges from 1:1 to 2:1.

The invention is based on the fact that using the process according to this invention, one can produce sodium lactamoaluminates during one operation step by adding slowly a sodium hydridoaluminate or sodium tetraamidoaluminate to an excess of a lactam. This reaction is accompanied by the evolution of hydrogen or ammonia. In this process, reduction not more than 1%, if any, takes place to corresponding azacycloalkanes which act as inhibitors of the polymerization of lactams.

From the economic point of view it is preferable to produce sodium lactamoaluminates from trisodium hexahydridoaluminate or sodium tetraamidoaluminate as the starting materials.

The sodium tetrahydridoaluminate and trisodium hexahydridoaluminate can be added to a lactam in the form of a suspension in an aromatic hydrocarbon which can be prepared by direct synthesis from sodium, aluminium, and hydrogen. No isolation of the hydrides from this reaction mixture is necessary to be made. When the reaction of the hydride suspension with a lactam is complete, the unreacted aluminium is filtered off and a solution of a sodium lactamoaluminate is obtained.

Sodium tetrahydridoaluminate can be added to a lactam also in the form of an ether solution. Alternatively, the reaction of sodium tetrahydridoaluminate with a lactam can be carried out in boiling solvent, this solvent being a mixture of an aromatic hydrocarbon and ether, and the sodium tetrahydridoaluminate is added via extraction made by reflux of the evaporated solvent. The sodium tetrahydridoaluminate feed rate is here controlled by the applied amount of ether.

Sodium dihydrido-bis(2-methoxyethoxo)aluminate, which is produced on an industrial scale, is mostly applied in the form of a toluene solution.

The starting sodium tetraamidoaluminate is prepared from sodium, aluminium, and ammonia by the method described by F. W. Bergstrom in J. Am. Chem. Soc. 45, 2788 (1923) and by R. Brec and J. Rouxel in C.R. Acad. Sci. Ser. C 264, 512 (1967).

The composition of the resulting product is determined by the selection of the starting aluminate. Using sodium dihydrido-bis(2-methoxyethoxo)aluminate alone, a sodium dilactamo-bis(2-methoxyethoxo)aluminate is produced. Application of sodium tetrahydridoaluminate, trisodium hexahydridoaluminate, or sodium tetraamidoaluminate results in a sodium tetralactamoaluminate. In case that sodium dihydrido-bis(2-methoxyethoxo)aluminate in mixture with at least one of the other aluminates is applied in the process, the resulting product is a sodium lactamoaluminate of the general formula $NaAl(OCH_2CH_2OCH_3)_xL_{4-x}$, where $x$ and L have the same meaning as mentioned before. The resulting composition of the product, i.e. the magnitude of the index $x$, is determined by the molar proportion of the starting aluminates, and sodium lactamoaluminates made thereof in the process, in accordance with the following equation:

$$x\,NaAl(OCH_2CH_2OCH_3)_2L_2 + (2-x)\,NaAlL_4 \rightarrow$$
$$\rightarrow 2\,NaAl(OCH_2CH_2OCH_3)_xL_{4-x}$$

The compounds produced in accordance with this invention are soluble in aromatic hydrocarbons and are applied as initiators of the anionic polymerization of lactams. Upon reaction with water present in lactams the sodium lactamoaluminates liberate the bonded lactam; hence, the polymerization performed with these compounds does not require strictly anhydrous medium, as it is the case with alkali metal lactamates.

Reaction conditions and operating techniques will be more readily understood by reference to the following examples which are merely illustrative and are not intended to limit the scope of the invention.

EXAMPLE 1

A 2-l. three-necked flask equipped with a stirrer, a reflux water condenser and a dropping funnel was charged in an inert atmosphere with 565 g (5 mole) of 6-caprolactam and 300 ml of toluene. To this mixture, a solution of 56.6 g of 98% sodium tetrahydridoaluminate (1.02 mole) in 350 ml of dimethoxyethane was added dropwise with stirring over a period of three hours. The reaction was accompanied by hydrogen evolution. After the solution had been added, the dropping funnel was rinsed with 60 ml of dimethoxyethane and the obtained solution was added to the reaction mixture. When the reaction was complete, the reaction solution was clear and slightly yellowish. This solution was concentrated by evaporating a portion of the solvent which resulted in 877.4 g of 57.5% solution of sodium tetracaprolactamoaluminate.

EXAMPLE 2

A 250-ml. flask equipped with an extraction head (sintered glass) fitted with a reflux water condenser was charged in an inert atmosphere with 51 g of pyrrolidone (0.6 mole), 30 ml of toluene, and 30 ml of tetrahydrofuran. The extraction head was charged with 5.7 g of 98% sodium tetrahydridoaluminate (0.103 mole). The reaction mixture was then brought to the boiling point and sodium tetrahydridoaluminate was added by a slow extraction. The reaction was accompanied by hydrogen evolution. When the charged amount of the sodium tetrahydridoaluminate was extracted off, a clear, slightly yellowish solution was obtained which after evaporating a portion of tetrahydrofuran weighed 76.3 g and contained 52% of sodium tetrapyrrolidonoaluminate.

EXAMPLE 3

A 500-ml. three-necked flask equipped with a stirrer, a reflux water condenser, and a dropping funnel was charged in an inert atmosphere with 98.5 g (0.5 mole) of 12-laurolactam and 120 ml of toluene. At the boiling point of the obtained solution, a solution of 5.4 g of 98% sodium tetrahydridoaluminate (0.098 mole) in 40 ml of dimethoxyethane was added dropwise with stirring over a period of 2 hours. The reaction was accompanied by hydrogen evolution. The resulting solution was clear and slightly yellowish. After evaporating a portion of the solvent, this solution weighed 190 g and contained 43% of sodium tetralaurolactamoaluminate.

EXAMPLE 4

A 250-ml. flask equipped with a stirrer and a reflux water condenser was charged with 50.5 g of 6-caprolactam (25% excess) and 25 ml of toluene. To this mixture, a suspension of 5.75 g of powdered 98% sodium tetrahydridoaluminate in 50 ml of toluene was added gradually over a period of 2 hours. The suspension of sodium tetrahydridoaluminate was maintained by continuous agitating and added through a polyethylene capillary tube by means of nitrogen pressure. The residual suspension was added after rinsing the vessel with 10 ml of toluene. In the course of the reaction hydrogen was evolved and heat was released. The procedure resulted in 135 g of a solution containing 38.9% of sodium tetracaprolactamoaluminate.

EXAMPLE 5

A 1000-ml. flask equipped with a stirrer, and a reflux water condenser was charged with 126 g of ω-laurolactam (20% excess) and 250 ml of benzene. To this mixture there was added with stirring 100 ml of of suspension containing 10.18 g of 89% trisodium hexahydridoaluminate obtained by direct synthesis from sodium, aluminium, and hydrogen. The suspension of the trisodium hexahydridoaluminate was added over a period of 2.5 hours by the same technique as described in Example 4. 20 ml of benzene was applied to rinse the residual suspension. After cooling, the reaction mixture was filtered and the filter cake was washed with 20 ml of benzene. The procedure resulted in 461 g of a solution containing 16.07% of sodium tetralaurolactamoaluminate.

EXAMPLE 6

68 g of γ-butyrolactam (15% excess) was placed in a 250-ml. three-necked flask equipped with a stirrer, a reflux water condenser, and a dropping funnel. A suspension of 11.72 g of 98.5% trisodium hexahydridoaluminate in 100 ml of toluene was prepared and added dropwise to the liquid lactam (30° C) over a period of 3 hours. The addition of the suspension to the reaction mixture was performed in the same way as described in Example 4. The residual trisodium hexahydridoaluminate was brought into the reaction by rinsing the funnel with 20 ml of toluene. In the course of the reaction hydrogen was evolved and heat was released. The procedure resulted in 174 g of a solution containing 25% of sodium tetrabutyrolactamoaluminate.

EXAMPLE 7

1709 g of 6-caprolactam and 600 ml of toluene was placed in a 6-l. three-necked flask equipped with a stirrer, a reflux water condenser, and a dropping funnel. To the obtained suspension, 1800 g of a reaction mixture resulted from direct synthesis of sodium tetrahydridoaluminate in toluene was added dropwise with stirring over a period of 3 hours. The abovementioned mixture contained 7.89% of sodium tetrahydridoaluminate, 2.1% of trisodium hexahydriodoaluminate, 3.36% of sodium dihydrido-bis(2-methoxyethoxo)aluminate, and 2.5% of aluminium and other solid impurities. The reaction occurring in the flask was accompanied by hydrogen evolution. After cooling, the resulting reaction mixture was filtered and the filter cake was washed with 200 ml of toluene. The described procedure resulted in 4100 g of a filtrate containing 2.16% of aluminium which corresponded to a mixture of dissolved sodium tetracaprolactamoaluminate (36.23%) and sodium dicaprolactamo-bis(2-methoxyethoxo)aluminate (3.08%), the yield being 99.5%.

EXAMPLE 8

A 6-l. three-necked flask equipped with an efficient stirrer, a reflux water condenser, and a 2-l. dropping funnel was charged with 1832 g of 6-caprolactam (20% excess with respect to the aluminate), and 830 ml of toluene. Over a period of 2.5 hours, 1949 g of a 70% toluene solution of sodium dihydrido-bis(2-methoxyethoxo)aluminate was added dropwise with stirring to the suspension of 6-caprolactam. In the course of the reaction hydrogen was evolved and the temperature of the reaction mixture raised up to 85° C. The procedure resulted in 4450 g of a clear solution containing 64.35% of sodium dicaprolactamo-bis(2-methoxyethoxo)aluminate.

EXAMPLE 9

225.4 g of α-pyrrolidone (γ-butyrolactam) (50% excess) was placed in a 1000-ml. flask equipped with an efficient stirrer, a reflux water condenser, and a dropping funnel, and fused on heating to 30° C. Over a period of 3 hours, 288.6 g of a 70% toluene solution of sodium dihydrido-bis(2-methoxyethoxo)aluminate was added gradually with stirring. In the course of the reaction hydrogen was evolved and the temperature of the reaction mixture raised up to 80° C. The described procedure resulted in 530 g of a clear solution containing 69.5% of sodium dibutyrolactamo-bis(2-methoxyethoxo)aluminate.

EXAMPLE 10

A 500-ml. three-necked flask equipped with an efficient stirrer, a reflux water condenser, and a dropping funnel was charged with 70 g of ω-laurolactam (20% excess), and 150 ml of benzene. To this mixture, 44.1 g of a 65% benzene solution of sodium dihydrido-bis(2-methoxyethoxo)aluminate was added dropwise over a period of two hours. The obtained solution weighed 300 g and contained 28.03% of sodium dilaurolactamo-bis(2-methoxyethoxo)aluminate.

EXAMPLE 11

A 0.5-l. three-necked flask equipped with a stirrer, a dropping funnel, and a reflux water condenser closed by a drying tube filled with solid potassium hydroxide was charged with 12.2 g of 97.5% sodium tetraamidoaluminate (0.1043 mole), and 25 ml of benzene. To this mixture there was added dropwise 196.5 g of a 30% benzene solution of 6-caprolactam (0.522 mole) and the resulting mixture was then heated for 0.5 hour on a boiling water bath. The reaction was accompanied by ammonia evolution. To completely remove the ammonia the reaction mixture was bubbled through for 20 minutes by 4 l of dry nitrogen. The described procedure resulted in 196 g of a 26.5% solution of sodium tetrakis-6-caprolactamoaluminate.

EXAMPLE 12

A 250-ml flask equipped with a stirrer, a dropping funnel, and a reflux water condenser closed by a drying tube filled with solid potassium hydroxide was charged with 6.35 g of 97.5% sodium tetraamidoaluminate (0.0596 mole), and 20 ml of benzene. Over a period of 50 minutes, 70.9 g of a 50% toluene solution of 4-butyrolactam (0.417 mole) was added dropwise to the mixture. The reaction mixture was then heated for 45 minutes in a boiling water bath. After cooling to 20° C, the mixture had been evacuated until the vacuum reached 20 torr. The described procedure resulted in 82.1 g of 23% solution of sodium tetrakis-4-butyrolactamoaluminate.

EXAMPLE 13

A 250-ml. flask equipped with a stirrer, a dropping funnel, and a reflux water condenser closed by a drying tube filled with solid potassium hydroxide was charged with 4.52 g of 97.5% sodium tetraamidoaluminate (0.0423 mole), and 20 ml of benzene. To this mixture, 115.7 g of a 32.5% benzene solution of 12-laurolactam (0.191 mole) was added dropwise over a period of 45 minutes. The reaction mixture was then heated for 45 minutes in a boiling water bath. After substituting a straight through condenser for the reflux one, 35 ml of benzene was distilled off from the reaction mixture. The described procedure resulted in 97 g of a 36.4% solution of sodium tetrakis-12-laurolactamoaluminate.

What we claim is:

1. A process of manufacturing sodium lactamoaluminates of the general formula $$Na\ Al\ (OCH_2CH_2OCH_3)_x\ L_{4-x},$$

wherein $x$ is a number ranging from 0 to 2 and L is a residue derived by splitting off an active hydrogen from a lactam having the formula

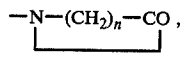

wherein $n$ is a number ranging from 3 to 11, which comprises: reacting a lactam of the formula LH, wherein L has the meaning as defined above, in an aromatic hydrocarbon medium with at least one compound selected from the group consisting of sodium tetrahydridoaluminate, trisodium hexahydridoaluminate, sodium dihydrido-bis(2-methoxyethoxo)aluminate, and sodium tetraamidoaluminate, wherein the molar ratio of the lactam to hydride hydrogen or to the NH$_2$ group in the aforementioned aluminates ranges from 1:1 to 2:1.

2. The process of claim 1 wherein the lactam is 6-caprolactam.

3. The process of claim 2 wherein the 6-caprolactam is reacted with sodium tetraamidoaluminate.

4. The process of claim 1 wherein the solvent is selected from the group consisting of benzene, toluene and mixtures thereof.

5. The process of claim 1 wherein the lactam is reacted with a composition selected from the group consisting of trisodium hexahydroaluminate and sodium tetraamidoaluminate.

6. The process of claim 1 wherein the aluminum containing composition is added incrementally to a mixture containing the lactam.

7. The process of claim 1 wherein the lactam is added incrementally to a mixture containing sodium tetraamidoaluminate.

8. The process of claim 1 wherein the lactam is selected from the group consisting of 6-caprolactam, pyrrolidone, 12-laurolactam, ω-laurolactam, γ-butyrolactam.

* * * * *